(12) United States Patent
Korsgaard

(10) Patent No.: US 7,423,121 B2
(45) Date of Patent: Sep. 9, 2008

(54) SODIUM CHANNEL RNA$_V$1.5A

(75) Inventor: Mads P. G. Korsgaard, Ballerup (DK)

(73) Assignee: Neurosearch A/S, Ballerup (DK)

( * ) Notice: Subject to any disclaimer, the term of this patent is extended or adjusted under 35 U.S.C. 154(b) by 604 days.

(21) Appl. No.: 10/311,255

(22) PCT Filed: Jun. 14, 2001

(86) PCT No.: PCT/DK01/00414

§ 371 (c)(1),
(2), (4) Date: Jun. 3, 2003

(87) PCT Pub. No.: WO02/02608

PCT Pub. Date: Jan. 10, 2002

(65) Prior Publication Data

US 2004/0106115 A1    Jun. 3, 2004

(30) Foreign Application Priority Data

Jul. 5, 2000    (DK) ............................... 2000 01049

(51) Int. Cl.
*C07K 14/00* (2006.01)
(52) U.S. Cl. ..................................................... 530/350
(58) Field of Classification Search ........................ None
See application file for complete search history.

(56) References Cited

U.S. PATENT DOCUMENTS

| | | | | |
|---|---|---|---|---|
| 5,380,836 | A * | 1/1995 | Rogart .......................... | 536/23.5 |
| 6,110,672 | A | 8/2000 | Mandel et al. | |
| 2004/0156859 | A1 * | 8/2004 | Ezrin et al. ................. | 424/185.1 |

FOREIGN PATENT DOCUMENTS

| | | |
|---|---|---|
| JP | 11-235186 A | 11/1999 |
| WO | WO 97/01577 A1 | 1/1997 |
| WO | WO 99/47670 A1 | 9/1999 |

OTHER PUBLICATIONS

Burgess, Daniel L., "Mutation of a new sodium channel, Scn8a, in the mouse mutant 'motor endplate disease", Nature Genetics, vol. 10, pp. 461-465, (1995).

Diss, J.K.J. et al, "Expression of skeletal muscle-type voltage-gated Na+ channel in rat and human prostate cancer cell lines", FEBS Letters, vol. 427, pp. 5-10, (1998).
Toledo-Aral, Juan J. et al., "Identification of PH1, a predominant voltage-dependant sodium channel expressed principally in peripheral neurons", Proc. Natl. Acad Sci., vol. 94, pp. 1527-1532, (1997).
Hainsworth, Atticus H. et al., "Sipatrigine (BW 619C89) is a Neuroprotective Agent and a Sodium Channel and Calcium Channel Inhibitor", CNS Drug Review, vol. 6, No. 2, pp. 111-134, (2000).
Lang, Daniel G. et al., "Lamotrigine , Phenytoin and Carbamazepine Interactions on the Sodium Current Present in N4TG1 Mouse Neuroblastima Cells", The Journal of Pharmacology and Experimental Therapeutics, vol. 266, No. 2, pp. 829-835, (1993).
Lu, Chiun-Mei et al., "Isolation of a Human-Brain Sodium-Channel Gene Encoding Two Isoforms of the Subtype III Alpha-Submit", Journal of Molecular Neuroscience, vol. 10, pp. 67-70, (1998).
Zona, Cristina et al., "Lamotrigine reduces voltage-gated sodium currents in rat central neurons in culture", Epilepsia, vol. 38, No. 5, pp. 522-525, (1997).
Rogart, R.B., "Molecular cloning of a putative tetrodotoxin-resistant rat heart Na+ channel isoform", Proc. Natl. Acad. Sci., vol. 86, pp. 8170-8174, (1989).
Hartmann, Hali A. et al, "Selective Localization of cardiac SCN5A sodium channels in limbic regions of rat brain", Nature Neuroscience, vol. 2, No. 7, pp. 593-595, (1999).
Korsgaard, M.P.G. et al., "Characterization of the novel voltage-gated Na+ channel rNa1.5a isolated from the rat hippocampal progenitor stem cell line HiB5" Gen Bank Accession No. AF353637, Feb. 27, 2001.
Korsgaard, Mad P.D., PHD Thesis entitled: "Molecular Cloning, Stable Expression and Pharmacological Characterization of Voltage-Gated Na+-Channels", Department of Medical Physiology, University of Copenhagen, Apr. 2001.
Plummer et al., "Evolution and Diversity of Mammalian Sodium Channel Genes," Genomics, vol. 57, pp. 323-331, 1999.

* cited by examiner

*Primary Examiner*—Michael Pak
(74) *Attorney, Agent, or Firm*—Birch, Stewart, Kolasch & Birch, LLP

(57) ABSTRACT

The present invention relates to a novel voltage gated sodium channel located in the brain, nucleotides coding for it, vectors and host cells containing the same, transgenic non-human animal capable of expressing the sodium channel, and methods of screening for modulators of the channel such as modulators for use in the treatment of seizures, and conditions related to the limbic system and limbic regions including limbic seizures.

7 Claims, No Drawings

SODIUM CHANNEL RNA$_V$1.5A

This application is the national phase under 35 U.S.C. § 371 of PCT International Application No. PCT/DK01/00414 which has an International filing date of Jun. 14, 2001, which designated the United States of America.

The present invention relates to a novel voltage gated sodium channel located in the brain, nucleotides coding for it, vectors and host cells containing the same, transgenic non-human animal capable of expressing the sodium channel, and methods of screening for modulators of the channel such as modulators for use in the treatment of seizures, and conditions related to the limbic system and limbic regions including limbic seizures.

Voltage-gated sodium channels are responsible for the rising phase of the action potential and play a role in a number of conditions related to a mediation of electrical activity in excitable tissues. A number of medicaments are known to act via a sodium channel including a number of cardiac drugs. The sodium channels known in the art include the major cardiac channel Na$_v$1.5 (formerly named H1 or SKM2) and the sensory neurone specific channel Na$_v$1.8 (formerly named SNS/PN3).

The present invention provides a new sodium channel located in the brain possible only located in the limbic system. More specially, the present invention relates to a voltage gated sodium channel from a rat astrocyte stemcell line called HiB5.

DESCRIPTION OF THE INVENTION

From a rat astrocyte stemcell line called HiB5 (Renfranz PJ, Cunningham MG & McKay RDG (1991) Region-specific differentiation of the hippocampal stem cell line HiB5 upon implantation into the developing mammalian brain. *Cell* (66) pp 713-29) a cDNA was cloned and the corresponding voltage gated sodium channel encoded by this sequence was characterised. The cDNA sequence exhibits a near 100% match to the heart specific sodium channel subtype rNa$_v$1.5 (GenBank Accession number M27902; formerly named rH1) but appears to be a splice variant since it lacks 159 nucleotides in position 3238 through 3396 relative to rNa$_v$1.5 coding sequence number. This corresponds to a deletion of 53 amino acids positioned intracellularly between domain II and III in the generally depicted structure of the α-subunit. In addition, a few bases differ between the two sequences but in a way that do not alter the amino acid sequence (see sequence SEQ No. 1).

By searching the GenBank using sequences surrounding the deleted area, no matches are returned supporting that this sequence is novel. As a control searching with the same sequence including the 159 bases, the subtype rNa$_v$1.5 is returned from GenBank.

The rNa$_v$1.5 subtype (gene locus: SCN5A) has been found to be expressed in the brain, restricted to the limbic regions (Hartmann, HA, Colom LV, Sutherland ML & Noebels JL (1999) Selective localization of cardiac SCN5A sodium channels in limbic regions of rat brain. *Nature neuroscience* (2), 7, pp 593-5). However, this work made use of probes for hybridisation and primers for polymerase chain reactions (PCR) that would not recognise the sodium channel according to the present invention, which is a splice variant of the cardiac sodium channel. In line with the nomenclature of this field, the present subtype is called rNa$_v$1.5a (or according to the former nomenclature rH1 A).

In a clinical perspective it should be noted that some complex seizure disorders are seeded in the limbic region. According to the present invention, conditions related to this region are of special interest, as it is believed that the specific channel according to the present invention plays an important role in this area.

Furthermore, it is relevant to point out that since rat and man have a very high sequence homology between other subtypes it is expected that a splice variant is also expressed in the limbic region of man. In addition, it has surprisingly been found that known anti-epileptic drugs like Lamotrigine (Lamictal) act more potently on the channel according to the present invention than on the classical brain subtype BIIA (for details, see Example 2) that they are thought to act on, so the anti-epileptic effect might be established via rNa$_v$1.5a.

Other indications with off spring in the limbic area may also be treated by modulation of rNa$_v$1.5a e.g. attention deficit, depression and other conditions including pain.

One aspect of the invention therefore provides an isolated nucleotide sequence wherein the sequence is as shown in SEQ No. 1 (rNa$_v$1.5a) or a variant thereof. In a further aspect, the invention relates to an isolated mammalian sodium channel protein encoded by the nucleotide sequence for rNa$_v$1.5a as shown in SEQ No. 1 or a variant thereof. In a still further aspect, the invention relates to an isolated mammalian brain sodium channel protein encoded by the sequence shown herein. In one embodiment, the isolated mammalian sodium channel or nucleotide sequence is isolated from the limbic region of a mammalian. Preferably, the sodium channel of the invention is isolated from the limbic region such as from the hippocampus. The sodium channel may be derived from any mammalian species, preferably from the rat or human. In a further embodiment, the invention relates to an isolated sodium channel derivable from the limbic region of a mammal, e.g. from a rat or human that has an IC$_{50}$ for Lamotrigine of less than 100 µM, preferably less than 50 µM, such as less than 25 µM, as measured in accordance with Example 2.

In a further aspect, the invention relates to a sodium channel protein or variant thereof as described above for use in a method for screening for agents acting as modulators on the sodium channel.

Included within the invention are variants of the sodium channel including fragments, analogues, derivatives and splice variants. The term variant refers to a protein or nucleotide sequence encoding a protein that retains substantially the same biological function or activity as the isolated sodium channel, rNa$_v$1.5a. The identity is preferably 99%, however even identity of 98, 97, 95, 90, and 80% is believed to provide a function comparable with the sodium channel isolated according to the invention. In one embodiment, the invention relates to an isolated nucleotide sequence having at least 98% identity with the sequence as shown in SEQ No. 1.

Analogues include precursor proteins or fusion proteins. Splice variants refer to a protein produced by the same gene, generated by alternative splicing of mRNA, that contains additions or deletions within the coding region. Splice variants that occur naturally are within the scope of the present invention.

Fragments also include portions of rNa$_v$1.5a, characterised by structural or functional attributes of the protein. Derivatives include naturally occurring allelic variants. Derivatives may also include non-naturally occurring proteins or fragments. Fragments may be fused or may be comprised within a larger protein or a precursor protein designed for expression in a host.

The invention also relates to antisense nucleotides or complementary strands to the sequence as disclosed herein as well as RNA, cDNA, genomic DNA and synthetic DNA that encode a mammalian sodium channel isolated from the limbic region of a mammal.

The nucleotide sequence of the present invention may be used for producing the sodium channel protein or variant thereof by recombinant techniques well known in the art.

Accordingly, in a further embodiment the present invention relates to a recombinant construct comprising the nucleotide sequence as described herein or variants thereof, an expression vector, such as a plasmid into which the sequence of the invention has been inserted, preferably, a promotor is operably linked to the sequence. Suitable vectors and promoters are known to the skilled person. In one embodiment, the invention relates to a recombinant polynucleotide comprising the nucleotide sequence as shown in SEQ No. 1 or a variant thereof. In a further embodiment, the invention relates to a vector, e.g. plasmid comprising a nucleotide sequence as described above. In a special embodiment, the invention relates to a vector wherein the nucleotide sequence is labelled with a detectable moiety. In a still further embodiment, the invention provides a host cell for example a higher eukayotic cell such as a mammalian cell or a lower eukaryotic cell. In a special embodiment, the invention relates to a host cell transfected with a vector as described above. In a further embodiment, the invention provides an immortalised mammalian cell line comprising the sequence as shown in SEQ No. 1 or a variant thereof.

The term isolate according to the present invention means that the material is removed from its original environment. The proteins and nucleotide sequences according to the present invention are also preferably provided in purified form and preferably to at least 50% purity, such as at least 75% purity, more preferred 90% purity, most preferred at least 95% purity such as 98% purity.

In a further aspect, the invention relates to a transgenic non-human animal comprising a diploid genome comprising a transgene including the sequence encoding as shown in SEQ No. 1 or a variant thereof and wherein the transgene is expressed to produce a sodium channel. In one embodiment, said sodium channel is expressed in an amount sufficient to be detectable in a brain homogenate of the transgenic animal. In a second embodiment, the animal is murine. In a further embodiment, the transgene is non-homologously integrated. In a still further embodiment, the expression of the sodium channel is under the control of a promotor sequence different from the promotor sequence controlling the transcription of the encoding sequence for the sodium channel.

In another embodiment, the present invention relates antibodies specific for the $rNa_v1.5a$. The antibody may be mono or polyclonal, may be intact antibody molecules or fragments containing the active binding region of the antibody. The antibody according to the present invention includes antibodies produced by well known techniques in the art. The antibodies of the invention may also be used for purifying the sodium channel of the present invention. In one embodiment, the invention relates to an antibody or fragment thereof which recognises and/or binds to a sodium channel encoded by the sequence as shown in SEQ No. 1 or a variant thereof. In another embodiment, the invention relates to an antibody obtained by means of an immune response to exposure to a substantially purified sodium channel encoded by the sequence as shown in SEQ No. 1 or a variant thereof. In a special embodiment, the antibody is monoclonal or polyclonal.

In an interesting aspect of the invention the sodium channel is used to identify or screen modulators of the channel. Different techniques known in the art may be utilised in this respect including patch clamp technology.

Thus, in a further aspect, the invention relates to a method for the identification of a modulator of a sodium channel encoded by the sequence as shown in SEQ No. 1 or a variant thereof comprising contacting said channel with a test compound and detecting activity or inactivity of said channel. In one embodiment, the invention relates to a method of assaying test compounds which modulate sodium flux comprising expressing a protein or variant thereof encoded by the sequence as shown in SEQ No. 1 or a variant thereof. In a special embodiment, the method involves utilising patch clamp technology. The test methods according to the present invention are very useful for identifying pharmaceutically active compounds useful for disease and condition of the brain. The new brain specific sodium channel provides an important tool for identifying components, known or developed in the future, which may have a selective effect on the brain, and especially on the limbic system. The diseases or conditions may in addition to convulsions include panic disorders, hyperactivity disorders, depression, obsessive compulsive disorders, dementia, memory deficits, attention deficit, obesity, anxiety, eating disorders, drug addiction and misuse, altered sexual drive. Parkinson's disease and Alzheimer's disease may also be treated with compounds having an effect on the sodium channel according to the invention. Furthermore, conditions related to visceral responses originating to the limbic system may also be prevented or treated by use of medicaments capable of modulate the sodium channel according to the present invention. Such visceral symptoms may include respiration, and gastrointestinal movements and secretion.

In a still further aspect, the invention relates to a method and diagnostic kit for identifying a disease or condition wherein the function of the sodium channel is altered. Such method or kit may involve a labelled antibody to the sodium channel of the present invention.

In a further aspect, the invention relates to a compound identified by any of the methods as described above. In one embodiment, the compound has an $IC_{50}$ which is at least 10 times smaller than the $IC_{50}$ for $rNa_v1.2a$ measured as disclosed in Example 2.

EXAMPLE 1

Preparation

To elucidate the subtype present in HiB5 cells after having detected specific sodium current by means of electrophysiological measurements, Reverse transcriptase-polymerase chain reaction (RT-PCR) was set up. For primer design alignment of five different subtypes was made including $rNa_v1.1$ (formely named rBI), $rNa_v1.2a$ (formerly named rBIIA), $rNa_v1.3$ (formerly named rBIII), $rNa_v1.4$ (formerly named rSkM1), $rNa_v1.5$ and $rNa_v1.7$ (formerly named rPN1). In regions of high homology, 6 sense and 6 antisense degenerated oligos (15-23mers) where designed and paired to amplify regions thas displayed less homology in the alignment. Fragments would range from 500-1000 basepairs. Template cDNA was made by RT-PCR with random hexamers on mRNA extracted using "mRNA capture Kit" from Boehringer Mannheim.

The RT-reaction was performed with Superscript II reverse transcriptase at 42° C. for 50 min. The PCR was performed with 1 unit DNApolymerase constituting Taq:Pwo in the ratio 9:1, 200 µM dNTP and 500 nM primer. The mix was melted at 94° C. for 1:30 and the cycled 15 times at 94° C. for 0:30, 45° C. for 0:30 and 72° C. for 1:30 followed by 10 times at 94° C. for 0:30, 45° C. for 0:30 and 72° C. for 2:30. Fragments were completed at 72° C. for 5:00.

Four fragments were obtained using this approach. Search against GenBank gave a match to rNa$_v$1.5. Four sets of rNa$_v$1.5-specific primers where then designed to amplify 4 overlapping fragments. The template for these reactions was cDNA made from total RNA ("RNeasy mini kit", Qiagen) using oligodT as primers for the first strand. Another RT-reaction was performed using random hexamers. Both were with Superscript II reverse transcriptase at 42° C. for 50 min. PCR amplification for the four fragments were carried out employing nested primer pairs to ensure specificity.

The first PCR was performed as: 94° C. for 1:30 and the cycled 15 times at 94° C. for 0:30, 45° C. for 0:30 and 72° C. for 1:30 followed by 10 times at 94° C. for 0:30, 45° C. for 0:30 and 72° C. for 2:30. Fragments were completed at 72° C. for 5:00.

The nested PCR was performed as: 94° C. for 2:30 and the cycled 10 times at 94° C. for 0:45, 55° C. for 0:45 and 72° C. for 3:00 followed by 15 times at 94° C. for 0:45, 55° C. for 0:45 and 72° C. for 4:00. Fragments were completed at 72° C. for 5:00.

All fragments were cloned in an in-house vector called pSwaS derived from PCR-script from Invitrogen. Plasmids were amplified in the *E. coli* strain XL1-B which were grown on agar plates over night at 37° C. Plasmid amplification was carried out using standard LB media for culture and purifications kit from Qiagen for retrievement of plasmid DNA. Integrety of the plasmid was checked with restriction enzymes and gel electrophoresis.

The four fragments positioned in each pSwaS vector were excised with restriction enzymes in overlapping regions and ligated to form to vectors, one containing the 5' half and the other containing the 3' half. The vectors were amplified in XL1-B and checked by restriction enzyme cleavage. The 5' half was excised and ligated into the vector containing the 3' half to give the entire coding sequence.

This plasmid was amplified in XL1-B. Following this the coding sequence was excised and subcloned into an in-house expression vector pNS1z. This plasmid was amplified in the *E. coli* strain SURE which has a lower copy number than XL1-B and a lower tendency to rearrangement of repetitive eukaryotic sequences like sodium channels.

Purified plasmid was used for transfecting HEK293 cell and Zeocin was added to the growth medium for selection of stabile clones. Stabile clones from the primary culture flask were transferred to deepwell plates and when confluency in the wells the cells were transferred to T25 culture flasks. Following 5 passages, Zeocin was omitted from the medium and expression of the channel was monitored electrophysiologically.

EXAMPLE 2

Comparison of the Inhibitory Effect of Lamotrigine on the Classical Brain Type rNa$_v$1.2a and the Sodium Channel Expressed Endogenously in HiB5 Cells (rNa$_v$1.5a)

Experiments were performed as whole-cell recordings in physiological saline with stimulation of the sodium channel every 5 second by stepping from a holding potential (e.g. −90 mV) to −10 mV and monitoration of the peak current as a function of the concentration of Lamotrigine added to the recording chamber.

This gave rise to these values:
  $IC_{50}$=500 µM for rNa$_v$1.2a
  $IC_{50}$=20 µM for rNa$_v$1.5a Recovery from inactivation is slowed by Lamotrigine more pronounced on HiB5 cells than on rNa$_v$1.2a. This is a parameter of use-dependent mode of action that is desirable in treating epilepsy and therefore supports the idea that the modulation of rNa$_v$1.5a is a key factor in treating epilepsy.

The invention claimed is:

1. An isolated mammalian sodium channel protein encoded by the nucleotide sequence for rNa$_v$1.5a as shown in SEQ. ID. NO: 1 or a sequence having at least 99% identity to SEQ ID NO: 1, wherein said isolated mammalian sodium channel protein conducts sodium ions across a membrane in a cell comprising said sodium channel protein.

2. An isolated mammalian sodium channel of claim 1, wherein the nucleotide sequence is isolated from the limbic region of the mammal.

3. The isolated sodium channel protein according to claim 1 for use in a method for screening for agents acting as modulators on the sodium channel.

4. An isolated sodium channel, according to claim 1, which is derivable from the limbic region of a mammal, that has an IC$_{50}$ for Lamotrigine of less than 100 μM.

5. The isolated mammalian sodium channel according to claim 4, having an IC$_{50}$ for Lamotrigine of less than 50 μM.

6. The isolated mammalian sodium channel according to claim 4, having an IC$_{50}$ for Lamotrigine of less than 25 μM.

7. The isolated mammalian sodium channel according to claim 4, isolated from rat.

* * * * *

SEQUENCE LISTING

<160> NUMBER OF SEQ ID NOS: 1

<210> SEQ ID NO 1
<211> LENGTH: 5901
<212> TYPE: DNA
<213> ORGANISM: Rattus norvegicus

<400> SEQUENCE: 1

```
atggcaaacc tcctgttacc tcggggcacc agcagcttcc gtaggttcac ccgggagtca      60
ctggcggcca tcgagaagcg aatggctgaa aagcaagccc gaggaggttc ggccacctca     120
caggagagcc gtgagggcct gcaggaggag gaggctcccc ggccccagct ggacctacag     180
gcctccaaaa agctgccaga tctctatggc aaccccacccc gagagctcat cggggagccc     240
ctggaagacc tggacccttt ctatagtacc cagaagacct tcatcgtgct gaataagggc     300
aaaaccatct tccggttcag tgccaccaat gccttgtatg tcctcagccc cttccacccc     360
gtgcgccgag cggccgtgaa gatcctggta cactcgctct ttagcatgct catcatgtgc     420
accatcctga ccaactgcgt gttcatggcc cagcacgacc ctccgccttg gaccaaatat     480
gttgagtaca cctttactgc catctacacc tttgagtctc tggtcaagat tctagctcga     540
ggcttctgcc tgcatgcatt caccttcctt cgggacccgt ggaactggct agacttcagt     600
```

-continued

```
gtgatcgtca tggcatacac aactgaattt gtggacctgg gcaatgtctc agccttacgc    660
accttccgag tcctccgggc cctgaaaact atatcggtca tttcaggcct gaagaccatc    720
gtgggagccc taatccagtc tgtgaagaaa ctggccgatg tgatggtcct cactgtcttc    780
tgcctcagtg tctttgccct cattggcctg cagctcttca tgggcaacct gaggcacaag    840
tgtgtgcgta acttcaccga gctcaatggc accaatggtt ccgtggaggc cgacggccta    900
gtctggaact ccctggacgt ctacctcaat gacccagcca attacctgct caagaatggc    960
accacggatg tgttactatg tgggaacagc tctgatgccg gacatgccc tgagggctat    1020 cggtgcctga aggcaggtga aacccagac acggttaca ccagcttcga ctccttcgcc    1080
tgggccttcc ttgcactctt ccgcctgatg acacaggact gctgggaacg cctataccag    1140
cagaccctga ggtccgcagg aaagatctac atgatcttct tcatgctcgt catctttctg    1200
ggctccttct acctggtgaa cttgatcctg ctgtggtgg ccatggccta cgaggagcaa    1260
aaccaagcca ccatcgccga gacgaagag aaggagaagc gcttccagga ggccatggag    1320
atgctcaaga aggaacacga ggctctcacc atcagggtg tggataccgt gtcccgtagc    1380
tctctggaga tgtctccttt ggccccagta accaaccatg agagaaagag caaaaggagg    1440
aaacgactat cttcagggac agaggatggt ggggatgaca ggctccccaa gtcggactca    1500
gaagatggtc ccagagcatt gaatcagctc agcctcaccc atgggctcag ccggacatcc    1560
atgaggcccc gctcgagccg agggagcatt ttcacgttcc gaagacgggga ccaaggctct    1620 gaggcggact cgcagatgac cgagaacagc actgcggggg agagcgagag ccaccgcaca    1680
tcgctgctgg taccctggcc cctgcgccat cccagcgccc aaggacagcc cggccctgga    1740
gcctcagctc ccggttacgt tctcaatggc aaaaggaaca gcaccgtgga ctgcaatggg    1800
gtggtttcct tgctgggggc aggtgacgca gaggccacct ccccagggag ctaccttctc    1860
cgccctatgg tgctggaccg accccccgac acgaccactc cgtcagagga gcccggtggg    1920
ccccagatgc tgacacctca ggctccgtgt gcagatggtt ttgaggagcc cggagcacgg    1980
caacgggcac tcagcgctgt cagtgtcctc accagtgccc tggaagagtt ggaggagtcc    2040
catcggaagt gtccaccatg ctggaaccgc tttgcccagc actacctcat ctgggagtgc    2100
tgtccactct ggatgtccat caagcagaag gtgaagtttg tggtcatgga cccatttgcc    2160
gacctcacta tcaccatgtg catcgtgctc aatacgctct tcatggctct ggagcattac    2220
aacatgacgg cagagtttga ggagatgctg caggtcggaa acctggtctt cacgggaatc    2280
ttcacagcgg agatgacctt caagatcatc gcccttgacc cctactacta cttccagcag    2340
ggctggaata tcttcgacag catcatcgtc atcctcagtc tcatggagct ggggctgtcc    2400
cgcatgggca acttgtctgt gctacgttcc ttccgtctgc tgcgggtctt caagctggcc    2460
aagtcctggc ccaccctgaa cacgctcatc aagatcatcg gaactccgt gggcgccctg    2520 gggaacctga cctggtgct ggccatcatc gtcttcatct tcgccgtggt gggcatgcag    2580
ctcttcggca agaactactc ggagctgagg caccgcatca gcgactccgg cctgctgccc    2640
cgctggcaca tgatggactt tttccacgcc ttcctcatca tcttccgcat cctctgtggg    2700
gagtggatcg agaccatgtg ggactgcatg gaggtgtctg gcagtcgct gtgcttgctg    2760 gtcttcctgc tcgtcatggt cattggcaac cttgtggtcc tgaatctctt cttggccttg    2820
ctgctcagct ccttcagcgc agacaacctc acagcccctg acgaggatgg ggagatgaac    2880
aacctccagc tggccctggc tcgcatccag aggggcctgc gctttgtcaa gcggaccacc    2940
tgggacttct gctgcgggat cctgcggcgg cgacctaaga agcccgcggc tcttgccacc    3000
```

-continued

```
cacagccagc tgcccagctg tatcaccgcc cccaggtccc caccaccccc agaggtggag    3060
aaggtgcccc cagcccgcaa ggaaacacga ttcgaggagg acaagcgacc cggccagggc    3120
acccctgggg attcggagcc tgtgtgtgtg cccatcgccg tggctgagtc agacactgaa    3180
gaccaggaag aggatgaaga aacagccttt ggcacagagg aagagtccag caaacagacc    3240
cctgaggaca gttactccga gggcagcaca gctgacatga ccaacaccgc cgacctcctg    3300
gagcaaatcc cagaccttgg tgaggacgtc aaggacccag aggactgctt tactgaaggc    3360
tgcgtccgac gctgtccctg ctgcatggta gacacaaccc agtccccagg gaaggtctgg    3420
tggcgattgc gcaagacctg ctaccgcatc gtggagcaca gctggttcga gactttcatc    3480
atcttcatga tcctgctcag cagtggagcg ctggccttcg aggacatcta cctggaggag    3540
cggaagacca tcaaggttct gctggagtac gcggacaaga tgttcaccta cgtctttgtg    3600
ttggagatgc tgctcaagtg ggtggcctac ggcttcaaga agtacttcac caacgcctgg    3660
tgctggctgg acttcctgat tgtggacgtc tcgctggtca gcctcgtggc aaacaccttg    3720
ggcttcgccg aaatgggtcc catcaagtca ctgaggacac tgcgtgcact tcgacccctg    3780
agggccttgt cgagatttga gggcatgcgg gtggtggtca atgcgctggt gggcgccatc    3840
ccctccatca tgaacgtcct cctcgtctgc ctcatcttct ggctcatctt cagcatcatg    3900
ggcgtgaacc tcttcgccgg aagttcggt aggtgcatca accagacaga aggggacctg    3960
cctctgaact acaccatcgt gaacaacaag agtgagtgcg agtccttcaa cgtgaccgga    4020
gagttgtact ggaccaaggt gaaggtcaac tttgacaacg tgggagccgg gtacctggcc    4080
ctcctgcagg tggcgacatt taaaggctgg atggacatca tgtatgcggc tgtggactcc    4140
agagggtatg aggagcagcc gcagtgggaa gacaacctct acatgtacat ctactttgtc    4200
gtcttcatca tcttcggctc cttcttcacc ctcaacctct tcatcggtgt catcattgac    4260
aacttcaacc agcagaagaa aaagttaggg ggccaggata tcttcatgac ggaggagcag    4320
aagaagtact acaatgccat gaagaagctg ggctccaaga accccagaa gcccatccca    4380 cggcccttga acaagtacca gggtttcata ttcgacattg tgaccaagca ggccttcgat    4440
gtcaccatca tgttcctcat ctgtttgaac atggtgacca tgatggtgga cagatgac    4500 cagagccctg agaaggtcaa catcttggcc aagatcaacc tgctcttcgt ggccatcttc    4560
acaggcgagt gtattgtcaa gatggctgcc ctgcgccact attacttcac caacagctgg    4620
aacatcttcg actttgtggt ggtcatcctc tccattgttg gcactgtcct ctccgacatc    4680
atccagaagt acttcttctc cccgacactc ttccgggtca tccgtctggc caggatcggc    4740
cgcatcctca ggctgatccg cggagccaag gggattcgca cgctgctctt cgccctcatg    4800
atgtccctgc ccgccctctt caacatcggc ctcctcctct tcctcgtcat gttcatctac    4860
tccatcttcg gcatggccaa cttcgcttac gtcaagtggg aggccggcat cgatgacatg    4920
ttcaacttcc agaccttcgc caacagcatg ctgtgcctgt tccagatcac cacatcagcc    4980
ggctgggacg gcctcctcag ccccatcctc aacacgggc ctccctactg cgaccccaac    5040
ctgcccaaca gcaacggctc ccgggggaac tgtgggagcc cggcggtggg catcctcttc    5100
ttcaccacct acatcatcat ctccttcctc atcgtggtca acatgtacat cgccatcatc    5160
ctcgagaact tcagcgtggc caccgaggag agcacagagc ccctgagcga ggacgacttc    5220
gacatgttct atgagatctg ggagaagttc gacccggagg ccacccagtt cattgagtat    5280 ctggcccctgt ccgactttgc agatgccttg tctgagccgc tccgcatcgc caaacccaac    5340
```

```
cagataagcc tcatcaacat ggatctgccc atggtgagcg gagaccgtat ccactgtatg    5400
gacatactgt tcgctttcac caagagggtg ctcggcgagt ctggggagat ggatgccctg    5460
aagatccaga tggaggagaa gttcatggcg gccaaccctt ccaagatctc ctacgagccc    5520
atcaccacca ccctgaggag aaagcacgag gaggtgtcgg ccacggtcat ccagcgtgcc    5580
ttccggaggc acctgctgca gcgctcggtg aagcatgcct cctttctctt ccgccagcaa    5640
gcgggcggca gtggcctctc cgacgaggat gcccctgagc gggagggcct catcgcctac    5700
atgatgaatg ggaacttctc tcggcgcagt gctccgctct ccagctcctc catctcctcc    5760
acgtccttcc ccccgtccta cgacagcgtc acgagagcca ccagtgataa cctcccggtg    5820
cgtgcgtctg actatagccg cagcgaagat cttgcagact tccctccatc tccagatagg    5880
gaccgagagt ctatcgtgtg a                                              5901
```